(12) United States Patent
Eisen

(10) Patent No.: US 8,220,643 B2
(45) Date of Patent: Jul. 17, 2012

(54) UREA SORBENT

(75) Inventor: Moris S. Eisen, Kyrat Tyvon (IL)

(73) Assignees: Fresenius Medical Care Holdings, Inc., Waltham, MA (US); The Technion Research and Development Foundation, Ltd., Haifa (IL)

( * ) Notice: Subject to any disclaimer, the term of this patent is extended or adjusted under 35 U.S.C. 154(b) by 398 days.

(21) Appl. No.: 12/479,513

(22) Filed: Jun. 5, 2009

(65) Prior Publication Data

US 2010/0230346 A1 Sep. 16, 2010

Related U.S. Application Data

(60) Provisional application No. 61/059,610, filed on Jun. 6, 2008.

(51) Int. Cl.
- *B01D 15/00* (2006.01)
- *B01D 24/00* (2006.01)
- *C08F 118/00* (2006.01)
- *C08F 116/34* (2006.01)
- *C08F 116/36* (2006.01)

(52) U.S. Cl. ............ 210/502.1; 526/304; 526/315; 526/316; 526/318; 526/321

(58) Field of Classification Search .......... 210/290, 210/502.1; 526/321, 318, 315, 316, 304
See application file for complete search history.

(56) References Cited

U.S. PATENT DOCUMENTS

| | | |
|---|---|---|
| 2005/0036983 A1 | 2/2005 | Simon et al. |
| 2005/0233003 A1 | 10/2005 | Goldshtein et al. |
| 2008/0029579 A1 | 2/2008 | Gammelin et al. |

FOREIGN PATENT DOCUMENTS

WO WO 02/40039 A2 5/2002

OTHER PUBLICATIONS

International Search Report, International Application No. PCT/US2010/037637, date of mailing Feb. 25, 2011.
Notification Concerning Transmittal of International Preliminary Report on Patentability for PCT/US2010/037637, date of mailing: Dec. 15, 2011 (6 pages).

*Primary Examiner* — John Kim
(74) *Attorney, Agent, or Firm* — Hamilton, Brook, Smith & Reynolds, P.C.

(57) ABSTRACT

A sorbent polymer is provided that interacts or reacts with aqueous urea to aid the regeneration of a dialysate liquid. The sorbent polymer may include one or more specific functional groups bonded thereto. Such specific functional groups are selected from carboxylic acids, carboxylic acid esters, carboxylates, amides, dicarboxylic acids, dicarboxylic acid esters, and dicer boxylates to produce the desired urea sorbent.

6 Claims, 1 Drawing Sheet

US 8,220,643 B2

UREA SORBENT

CROSS-REFERENCE TO RELATED APPLICATIONS

This application claims priority from U.S. Provisional Patent Application No. 61/059,610, filed Jun. 6, 2008 and entitled UREA SORBENT, which is incorporated herein by reference.

TECHNICAL FIELD

The following disclosure relates to sorbent materials for separating and/or removing urea from dialysate solutions in sorbent-based dialysis treatment or for separating and/or removing urea form aqueous solutions or liquids in medical related processes or circumstances.

BACKGROUND

Homodialysis is a process by which toxin and other molecules, such as urea, are removed from the blood using a semi-permeable filtering membrane. Typically, the patient's blood and an aqueous solution (i.e., dialysate) are pumped in counter-direction flows in and about hollow, semi-permeable fibers. In FIG. 1 a known configuration of a dialyzer is shown. Generally, blood flows in one end of the dialyzer and through hollow semi-porous or semi-permeable fibers toward the blood output side of the dialyzer. Meanwhile, dialysate flows in an opposite direction, with respect to the blood flow, by entering a dialysate inlet and flowing around or about the semi-porous hollow fibers in which the blood is flowing. The dialysate then exits the dialysate outlet. The toxins within the blood are removed from the blood via a combination of diffusion, convection, and osmosis processes while the blood is flowing within the fibers and the dialysate is flowing outside the fibers. Generally, the dialyzer is comprised of a large number of semi-permeable hollow fibers bundled together and placed in a cylindrical jacket as shown. Present day dialysis processes may be classified as: 1) single pass; and 2) sorbent-based. Single pass processes require a continuous supply of gallons of fresh and treated water. The treated water may be purified by for example, reverse osmosis or distillation. The gallons of fresh and treated water are used to create the dialysis fluid, which is discarded after flowing through the dialyzer and collecting the toxins in a single pass through of the dialyzer.

FIG. 2 shows a schematic/diagram of a cross section of a single semi-permeable fiber that may be used in a dialyzer. The blood flows through the hollow lumen within the semi-permeable walls of the fiber. The membrane walls have a thickness, which is the difference of the radius R2 minus the radius R1. The membrane is semi-permeable and the dialysate, as shown, flows in the opposite direction outside of the semi-permeable fiber.

Sorbent dialysis differs from single pass dialysis in that the dialysate is regenerated using a series of chemical powders to remove toxins from the dialysate solution. Typically, spent dialysate from the dialyzer is pumped through the first chemical layer of an enzyme called "urease". The urease catalyzes the breakdown of urea into ammonia and carbon dioxide. The dialysate will then pass through a second chemical layer, a cation exchange layer (zirconium phosphate) which absorbs ammonia and other positively charged ions and then through a third chemical layer, an anion exchange layer (hydrous zirconium oxide) where anions such as phosphate and fluoride are absorbed. Finally, the dialysate is pumped through a fourth layer of activated carbon where organic metabolites such as creatinine are absorbed. At some point, the filtered dialysate may be passed through a degasser to remove air, carbon dioxide and other gas bubbles that may form or be found in the dialysate.

The capacity of the zirconium phosphate cation exchange layer to absorb ammonia is limited by the number of sites available to bind ammonia. If the zirconium phosphate layer is depleted, ammonia will remain in the dialysate as it is recycled to the dialyzer. In this case the patient may be at risk of ammonia toxicity. Consequently, the filtered dialysate must be periodically tested or monitored for ammonia concentration.

A typical dialysis patient generates an excess of about 24 to about 60 grams of urea per day that must be removed from the blood to avoid uremia. Therefore, what is needed is a sorbent for use in dialysis that has the capacity to remove this quantity of urea in a reasonable time frame. Thus, suitable sorbents should have the capacity to remove approximately 2.5 grams per deciliter of dialysate per hour (gm/dl/hr) from the dialysate.

SUMMARY

In one embodiment, a urea sorbent is provided that is suitable for use in a sorbent-based dialysis process. The sorbent absorbs urea from the dialysate without generating ammonia or carbon dioxide, thereby eliminating the need for monitoring the concentration of ammonia in the dialysate as well as reducing or eliminating the need for de-gassing the dialysate. In one variation, the sorbent is insoluble or substantially insoluble in water and effective to remove urea from dialysate in a pH range of between 4 and 12 and more particularly in a pH range of between about 6 and 8. In another embodiment the sorbent is soluble or substantially soluble and effective to bond with urea to remove, or bound urea from a dialysate solution or other aqueous solution.

In another aspect, a filter for regenerating dialysate includes a sorbent layer comprising a polymer having specific functional groups bonded thereto that interact or react with urea at a pH of between 4 and 12, and more particularly at a pH of between 6 and 8, to remove urea from an aqueous solution. The exemplary polymer may be any one of soluble, substantially soluble, insoluble and substantially insoluble in water. The exemplary polymer further reacts or interacts with urea while near room temperature or while in a defined temperature range between about 50° F. and 110° F. without releasing ammonia or generating carbon dioxide. The reaction product of the polymer and urea may also be any one of soluble, substantially soluble, insoluble and substantially insoluble in water. A second filter layer may be used with the exemplary polymer sorbent. The second filter layer comprises activated carbon for absorbing organic metabolites from the dialysate or other aqueous solution. In one variation, the filter further includes an anion exchange layer for removing anions from the dialysate.

In another aspect, a filter for removing urea from an aqueous solution or liquid is provided. The filter comprises a sorbent layer or coating. The sorbent layer or coating comprises a polymer having specific functional groups bonded thereto. The exemplary polymer having specific functional groups bonded thereto interacts or reacts with urea at a pH of between 4 and 12 or a predetermined bounded pH range therebetween (i.e., 3 to 7, 5-9, 6-8, etc.) Upon interaction or perhaps a reaction with urea, urea is bonded to the exemplary sorbent polymer and removed from an aqueous solution. An exemplary polymer may be soluble, substantially soluble, insoluble, or substantially insoluble in water. Furthermore, an exemplary polymer reacts with urea at near room temperature or other predetermined temperature range without releasing ammonia or generating carbon dioxide. In various aspects, an exemplary polymer reacts or interacts with urea to produce a single reaction product. The filter may also include activated carbon for adsorbing and removing other molecules from the aqueous solution. The reaction product produced by the reaction or interaction of an exemplary polymer and urea may be soluble, substantially soluble, insoluble, or substantially insoluble in water.

BRIEF DESCRIPTION OF THE DRAWINGS

For a more complete understanding, reference is now made to the following description taken in conjunction with the accompanying Drawings in which.

DETAILED DESCRIPTION

Figure 1:
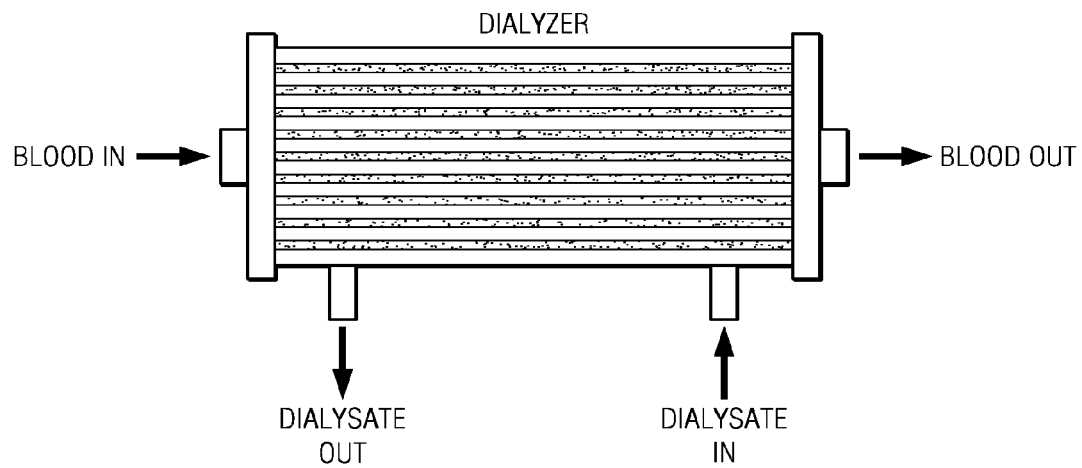
FIG. 1 illustrates a diagram of a dialyzer.
Figure 2:
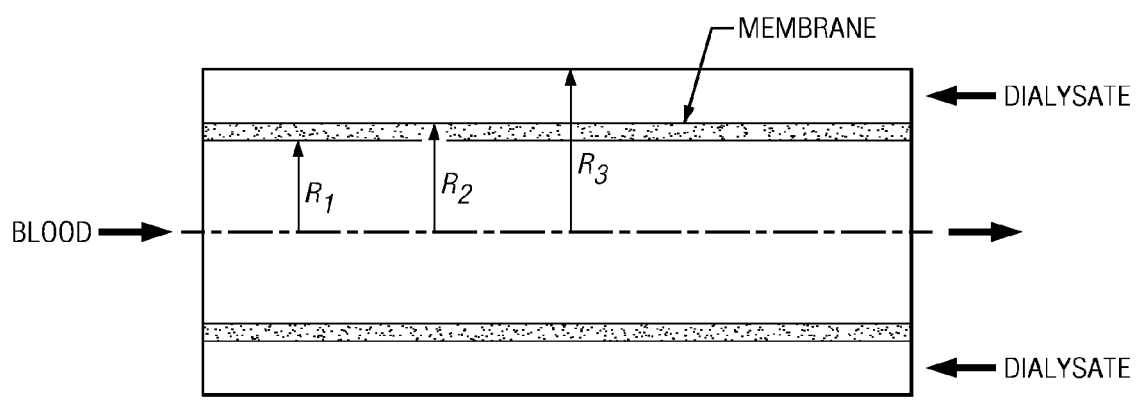
FIG. 2 illustrates a cross-sectional diagram of a fiber lumen in a dialyzer.

Referring now to the drawings, the various views and embodiments of exemplary urea sorbents are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Sorbent Preparation:

1. Preparation of MPS-IV-048 (polyvinylglyoxalate)

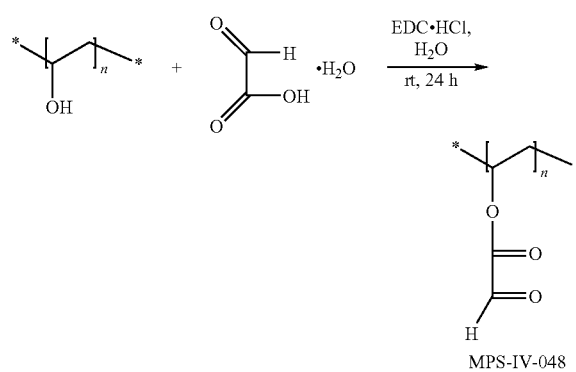

1.1 Reagents

| Entry | Reagent/solvent | Amount | mmol | Equivalent |
|---|---|---|---|---|
| 1 | Polyvinyl alcohol (M. wt. = 205000) | 1.000 g | $5.0 \times 10^{-3}$ (23.3 mmol of alcohol units) | 1 |
| 2 | Glyoxylic acid monohydrate (M. wt. = 92) | 2.144 g | 23.30 | 1 |
| 3 | EDC•HCl (M. wt. = 191.71) | 3.973 g | 20.72 | 0.88 |
| 4 | Distilled water | 15 ml | | |

1.2 Procedure.

To a stirred solution of glyoxylic acid monohydrate and EDC.HCl in distilled water, polyvinyl alcohol was added stirred the solution for 24 h. Water was evaporated under reduced pressure to obtain a gum, which was used for urea trapping experiments from the dialysis solutions.

2. Preparation of MPS-IV-054 (polyvinylglyoxalate)

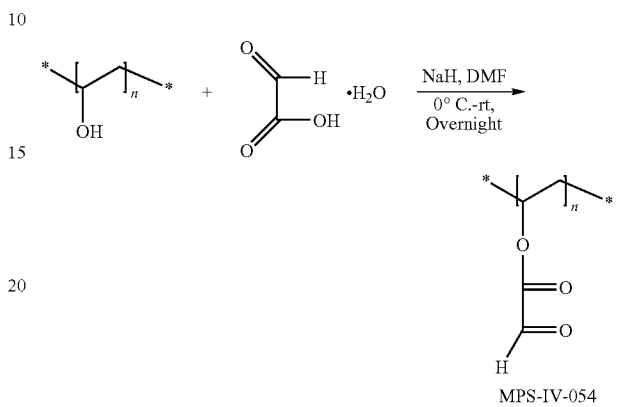

2.1 Reagents

| Entry | Reagent/solvent | Amount | mmol | Equivalent |
|---|---|---|---|---|
| 1 | Polyvinyl alcohol (M. wt. = 205000) | 1.000 g | $5.0 \times 10^{-3}$ (23.3 mmol of alcohol units) | 1 |
| 2 | Glyoxylic acid monohydrate (M. wt. = 92) | 2.144 g | 23.30 | 1 |
| 3 | NaH (M. wt. = 24 55-60% in suspension) | 1.538 g | 0.846 | 1.51 |
| 4 | Dry-N,N-Dimethylformamide (DMF) | 10 ml | | |

2.2 Procedure

Sodium hydride was added to a cooled (0° C., ice bath) stirred suspension of polyvinyl alcohol in dry DMF and stirring continued for 2-3 min. Glyoxylic acid monohydrate was added to this mixture and the mixture was brought to room temperature after 2 h stirring at 0° C. Stirring continued for overnight. The solid obtained was washed with DCM and used for urea trapping experiments from the dialysis solutions.

2.3 Properties

Weight of MPS-IV-054=3.691 g

Melting Point of MPS-IV-054=doesn't melt up to 290 0° C.

Mn=75540; Mw=79736; p=1.055 g/cm³

3. Preparation of MPS-V-003 (Bis(polyvinyloxalate))

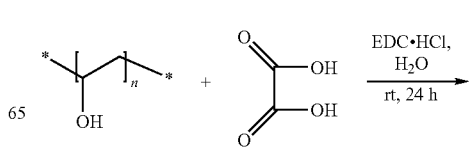

3.1 Reagents

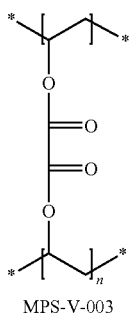

MPS-V-003

| Entry | Reagent/solvent | Amount | mmol | Equivalent |
|---|---|---|---|---|
| 1 | Polyvinyl alcohol (M. wt = 205000) | 1.000 g | $5.0 \times 10^{-3}$ (23.3 mmol of alcohol units) | 1 |
| 2 | Oxalic acid (M. wt. = 78) | 2.000 g | 25.64 | 1.1 |
| 3 | EDC•HCl (M. wt. = 191.71) | 3.973 g | 20.72 | 0.88 |
| 4 | Distilled water | 20 ml | | |

3.2 Procedure

To a stirred solution of oxalic acid and EDC.HCl in distilled water, polyvinyl alcohol was added stirred the solution for 24 h. Water was evaporated under reduced pressure to obtain a gum, which was used for urea trapping experiments from the dialysis solutions.

3.3 Properties

Weight of MPS-V-003=6.20 g

4. Preparation of MPS-V-004 (polyvinylpyruvate)

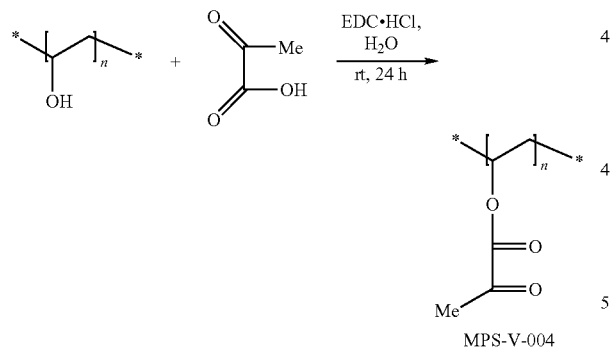

MPS-V-004

4.1 Reagents

| Entry | Reagent/solvent | Amount | mmol | Equivalent |
|---|---|---|---|---|
| 1 | Polyvinyl alcohol (M. wt. = 205000) | 1.000 g | $5.0 \times 10^{-3}$ (23.3 mmol of alcohol units) | 1 |
| 2 | Pyruvic acid (M. wt. = 88.06; d = 1.06) | 2.10 ml (≡2.226 g) | 25.28 | 1.1 |
| 3 | EDC•HCl (M. wt. = 191.71) | 3.92 g | 20.44 | 0.88 |
| 4 | Distilled water | 15 ml | | |

4.2 Procedure

To a stirred solution of pyruvic acid and EDC.HCl in distilled water, polyvinyl alcohol was added stirred the solution for 24 h. Water was evaporated under reduced pressure to obtain a gum, which was used for urea trapping experiments from the dialysis solutions.

4.3 Properties

Weight of MPS-V-004=6.42 g

5. Preparation of MPS-V-005 (polyvinylbezoate0.33 polyvinylalcohol0.66)

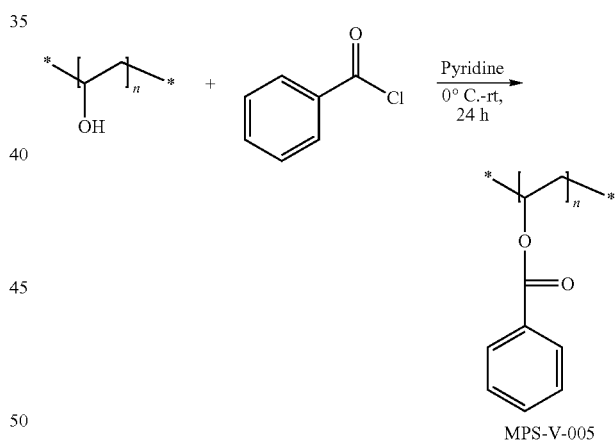

MPS-V-005

5.1 Reagents

| Entry | Reagent/solvent | Amount | mmol | Equivalent |
|---|---|---|---|---|
| 1 | Polyvinyl alcohol (M. wt. = 205000) | 2.000 g | $1.0 \times 10^{-2}$ (46.6 mmol of alcohol units) | $4 \times 10^{-2}$ (46.6 mmol of alcohol units) | 1 |
| 2 | Benzoyl chloride (M. wt. = 130.57; d = 1.211) | 2.00 ml (≡2.422 g) | 17.23 | 0.37 |
| 3 | Dry pyridine | 25 ml | | |

5.2 Procedure

To a stirred, cooled (0° C., ice bath) solution of polyvinyl alcohol in dry pyridine (17 ml), a solution of benzoyl chloride in dry pyridine (8 ml) was added dropwise over a period of 10 min and stirring continued for 24 h with gradual increase in reaction temperature to rt. After 24 h, the pyridine was removed under reduced pressure and by co-evaporation with toluene to obtain a gum which was used for next step. The gum (MPS-V-005) swelled when brought in contact with solvents like ethyl acetate, dichloromethane (DCM), chloroform and methanol.

6. Preparation of MPS-IV-009 (polyvinylbezoate0.33 polyvinylglyoxalate0.66)

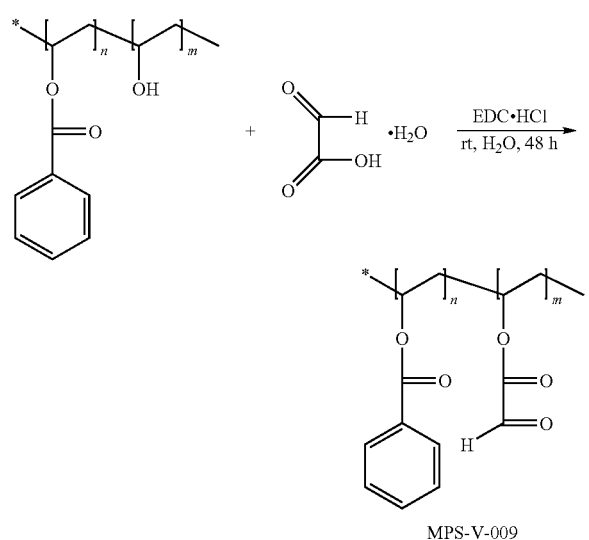

MPS-V-009

6.1 Reagents

| Entry | Reagent/solvent | Amount | mmol | Equivalent |
|---|---|---|---|---|
| 1 | MPS-V-005 | 2.000 g | (29.3 mmol of alcohol units) | 1 |
| 2 | Glyoxylic acid monohydrate (M. wt. = 92) | 0.920 g | 10.00 | 0.34 |
| 3 | EDC•HCl (M. wt. = 191.71) | 1.55 g | 10.00 | 0.34 |
| 4 | Distilled water | 20 ml | | |

6.2 Procedure

A solution of glyoxylic acid monohydrate and EDC.HCl in distilled water was added to MPS-V-005 and the suspension was stirred at room temperature for 48 h. The white ppt obtained was filtered off, dried and used for urea trapping experiments from the dialysis solutions.

6.3 Properties

Weight of MPS-V-009=1.543 g

7. Preparation of MPS-V-027 (polyvinylglyoxalate-ethylene copolymer)

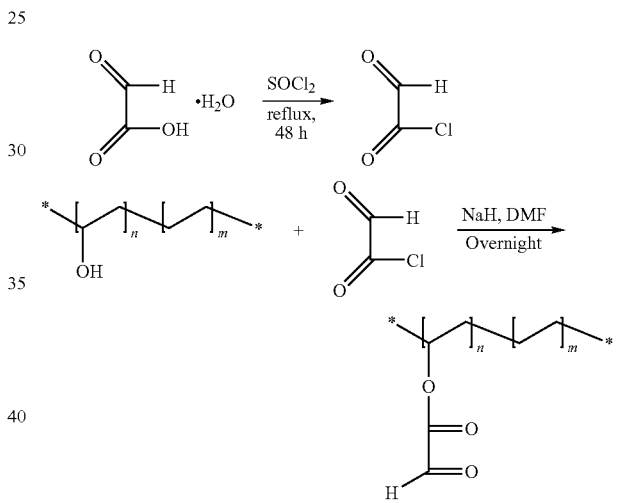

MPS-V-027

7.1 Reagents

| Entry | Reagent/solvent | Amount | mmol | Equivalent |
|---|---|---|---|---|
| 1 | Polyvinyl alcohol-coethylene (27% ethylene) | 2.28 g (= 1.838 g of polyvinyl alcohol) | 41.67 mmol of OH group | 1 |
| 2 | Glyoxalic acid monohydrate (M. wt. = 92) | 4.00 g | 43.48 | 1.04 |
| 3 | NaH (M. wt. = 24 55-60% in suspension) | 1.200 g | 50.00 | 1.2 |
| 4 | Thionyl chloride (M. wt. = 118.97, d = 1.613) | 12 ml (≡19.572 g) | 164.51 | 3.78 |
| 5 | Dry-N,N-Dimethylformamide (DMF) | 30 ml | | |

7.2 Procedure

Glyoxylic acid monohydrate was dissolved in thionyl chloride and the mixture was refluxed for 48 h. Removal of excess thionyl chloride under vacuum gave a gum (glyoxaloyl chloride). Polyvinyl alcohol co-ethylene was dissolved in dry DMF (by warming up to 100° C.) and this solution was added (after cooling to about 40° C.) to the previously obtained gum. The mixture was stirred for about 30 min in ice bath and NaH was added. Stirring continued for overnight after removal of the ice bath to obtain a sticky solid which was used for the urea trapping experiments from the dialysis solutions.

7.3 Properties

Weight of MPS-V-027=4.763 g

8. Preparation of MPS-V-036 (polyacrylicacid$_{0.9}$polyvinylpolyacrylicacid$_{0.1}$)

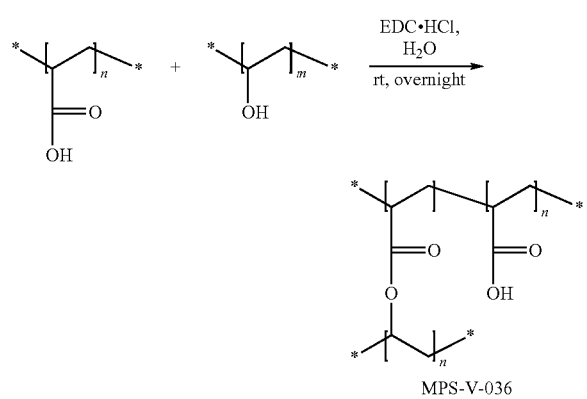

8.1 Reagents

| Entry | Reagent/solvent | Amount | mmol | Equivalent |
|---|---|---|---|---|
| 1 | Poly (acrylic acid) (M. wt. = 4000000) | 1.500 g | $3.75 \times 10^{-4}$ (20.83 mmol of —COOH units) | 1 |
| 2 | Polyvinyl alcohol (M. wt. = 205000) | 1.000 g | $4.88 \times 10^{-4}$ (2.27 mmol of —OH units) | 0.1 |
| 3 | EDC•HCl (M. wt. = 191.71) | 0.479 g | 2.49 | 1.1 eq of —OH groups |
| 4 | Distilled water | 50 ml | | |

8.2 Procedure

Poly(acrylic acid) was added to a stirred solution of EDC.HCl in distilled water. To this stirred suspension, polyvinyl alcohol was added and the solution was stirred for overnight. The gel obtained was filtered under suction (vacuum pump), washed with water, methanol, dichloromethane (DCM), acetone and ether respectively and dried for one week at room temperature to obtain a glassy solid, which was used for urea trapping experiments from the dialysis solutions.

8.3 Properties

Weight of MPS-V-036=3.361 g

9. Preparation of MPS-V-037 (polyvinylpyrurate-ethylene copolymer)

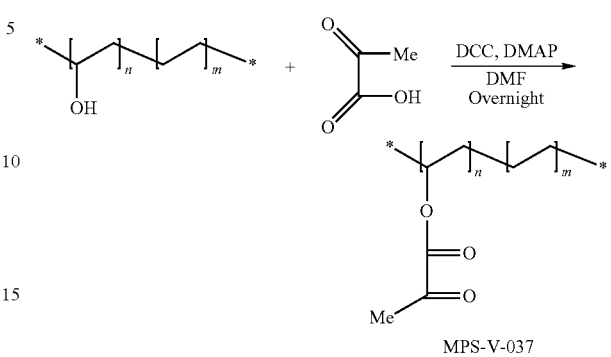

9.1 Reagents

| Entry | Reagent/solvent | Amount | mmol | Equivalent |
|---|---|---|---|---|
| 1 | Polyvinyl alcohol-coethylene (27% ethylene) | 1.14 g (=0.909 g of polyvinyl alcohol) | 20.84 mmol of OH group | 1 |
| 2 | Pyruvic acid (M. wt. = 88.06, d = 1.26) | 1.90 ml (=2.394 g) | 27.19 | 1.3 |
| 3 | DCC (M. wt. = 206.33) | 6.450 g | 31.26 | 1.5 |
| 4 | DMAP (M. wt. = 122.17) | 0.382 g | 3.13 | 0.15 |
| 5 | Dry-N,N-Dimethylformamide (DMF) | 30 ml | | |

9.2 Procedure

Polyvinyl alcohol co-ethylene was dissolved in DMF (15 ml) by heating the mixture to 100° C. This solution (after cooling to 40° C.) was added to a mixture of pyruvic acid, dicyclohexyl carbodiimide (DCC) and 4-dimethylaminopyridine (DMAP) in dry DMF (15 ml) and the reaction mixture was stirred at room temperature for overnight. The solid obtained was filtered off, washed with water, methanol, dichloromethane (DCM), acetone and ether respectively, dried and used for the urea trapping experiments from the dialysis solutions.

9.3 Properties

Weight of MPS-V-037=6.305 g

10. Preparation of MPS-V-038 (polyvinylglyoxalate-ethylene copolymer)

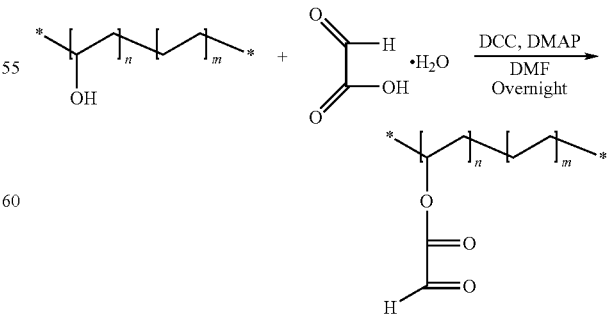

10.1 Reagents

| Entry | Reagent/solvent | Amount | mmol | Equivalent |
|---|---|---|---|---|
| 1 | Polyvinyl alcohol-coethylene (27% ethylene) | 1.14 g (≡0.909 g of polyvinyl alcohol) | 20.84 mmol of OH group | 1 |
| 2 | Glyoxylic acid monohydrate (M. wt. = 92) | 2.400 g | 26.09 | 1.25 |
| 3 | DCC (M. wt. = 206.33) | 6.450 g | 31.26 | 1.5 |
| 4 | DMAP (M. wt. = 122.17) | 0.382 g | 3.13 | 0.15 |
| 5 | Dry-N,N-Dimethylformamide (DMF) | 30 ml | | |

10.2 Procedure

Polyvinyl alcohol co-ethylene was dissolved in DMF (15 ml) by heating the mixture to 100° C. This solution (after cooling to 40° C.) was added to a mixture of glyoxylic acid monohydrate, dicyclohexyl carbodiimide (DCC) and 4-dimethylaminopyridine (DMAP) in dry DMF (15 ml) and the reaction mixture was stirred at room temperature for overnight. The solid obtained was filtered off, washed with water, methanol, dichloromethane (DCM), acetone and ether respectively, dried and used for the urea trapping experiments from the dialysis solutions.

10.3 Properties

Weight of MPS-V-038=6.025 g

11. Preparation of MPS-V-047 (isopropylaminepolyacrylicamide)

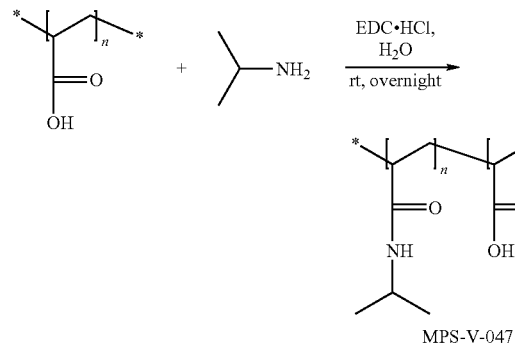

11.1 Reagents

| Entry | Reagent/solvent | Amount | mmol | Equivalent |
|---|---|---|---|---|
| 1 | Poly (acrylic acid) (M. wt. = 4000000) | 1.500 g | $3.75 \times 10^{-4}$ (20.83 mmol of —COOH units) | 1 |
| 2 | iso-Propylamine (M. wt. = 59.11, d = 0.688) | 0.20 ml (≡0.138 g) | 2.33 | 0.11 |
| 3 | EDC•HCl (M. wt. = 191.71) | 0.479 g | 2.49 | 1.1 eq of —OH groups |
| 4 | Distilled water | 50 ml | | |

11.2 Procedure

Poly(acrylic acid) was added to a stirred solution of EDC.HCl in distilled water. To this stirred suspension, isopropylamine was added and the solution was stirred for overnight. The gel obtained was filtered under suction (vacuum pump), washed with water, methanol, dichloromethane (DCM), acetone and ether respectively and dried for one week at room temperature to obtain a thick gel (like a glassy solid), which was used for urea trapping experiments from the dialysis solutions.

11.3 Properties

Weight of MPS-V-047=2.46 g

Dialysate solutions were analyzed for nitrogen content and the amount of urea in the dialysate was calculated. In some cases, additional urea was added to the solution as indicated in column 2 of each Table (1-5). The polymer reagent was added to the solution in the amount indicated in column 3. The mixture was stirred at room temperature for one hour and filtered. The filtrate was analyzed and the amount of urea removed from the dialysate solution was determined. A minus sign (−) indicates that the results were inconclusive.

In the following tables, the title identifies the particular polymer reagent tested. The first column of each table represents the experiment or run number. The second column identifies the particular dialysate solution used for the experiment and whether additional urea was added to the solution. The third column indicates the amount of polymer reagent used in the experiment. The fourth column gives the reaction conditions e.g. time and temperature. (Note: rt=room temperature). It is further understood that room temperature is between about 60 and 78° F. (about 15.56° C. to about 25.56° C.) and that reactions will also occur in a temperature range of between about 50° F. to about 110° F. (about 10° C. to about 43.3° C.). It is believed that reactions will also occur at colder or warmer temperatures, but such reactions have not been specifically tested. The fifth column identifies the analyzed portion of the reaction mixture (e.g. filtrate). In some cases, a neutralizing agent was added to the filtrate. The sixth column (BUN or Blood Urea Nitrogen) provides the concentration of nitrogen in the particular dialysate solution used for the experiment. The seventh column gives the amount of urea in the solution. The eighth column contains the maximum amount of urea in the solution. In the cases where additional urea was added as indicated in column 2, this number will be higher than the corresponding entry in the sixth column. The ninth column is the amount of urea removed from the dialysate solution. The first row of each table provides the nitrogen, urea and maximum or total amount of urea present in the dialysate solution used in the experiments.

TABLE 1

MPS-IV-048

| | | | | | Results (in mg/dL) | | | |
|---|---|---|---|---|---|---|---|---|
| Entry | Soln compn | Amount of Reagent Used (g) | Reaction condn. | Analyzed portion of reaction mixture | Blood Urea Nitrogen (BUN) | Blood Urea (BUN × 2.14) | Maximum amount of urea present | Amount of urea taken out (mg/dL/h) |
| 1 | Soln-3 Blank (10 ml) | — | — | — | 7.8 | 16.692 | 16.692 | — |

TABLE 1-continued

MPS-IV-048

| Entry | Soln compn | Amount of Reagent Used (g) | Reaction condn. | Analyzed portion of reaction mixture | Results (in mg/dL) | | | Amount of urea taken out (mg/dL/h) |
|---|---|---|---|---|---|---|---|---|
| | | | | | Blood Urea Nitrogen (BUN) | Blood Urea (BUN × 2.14) | Maximum amount of urea present | |
| 2 | Soln-3 (10 ml) | 2 | rt, 1 h | Filtrate (8 mL) | 14.6 | 31.244 | 16.692 | (−) 14.552 |
| 3 | Soln-3 (20 ml) + Urea (0.50 g) | 13 (0.50 g) | rt, 1 h | Filtrate (10 ml) | 797.2 | 1706.0 | 2516.7 | 810.7 |

TABLE 2

MPS-IV-054 and MPS-V-009

| Entry | Soln compn | Amount of Reagent Used (g) | Reaction condn. | Analyzed portion of reaction mixture | Results (in mg/dL) | | | Amount of urea taken out (mg/dL/h) |
|---|---|---|---|---|---|---|---|---|
| | | | | | Blood Urea Nitrogen (BUN) | Blood Urea (BUN × 2.14) | Maximum amount of urea present | |
| 1 | Soln-3 Blank (10 ml) | — | — | — | 4 | 8.56 | 8.56 | — |
| | | | | MPS-IV-054 | | | | |
| 2 | Soln-3 (20 ml) + Urea (0.50 g) | 2.5 | rt, 1 h | Filtrate (5 ml; pH = 10) | 2227 | 4765.78 | 5008.56 | 242.78 |
| 3 | Soln-3 (10 ml) + Urea (1.00 g) | 2.50 | rt, 1 h | Filtrate (3 ml; pH = 10) + 2% HCl- (0.4 ml) to neutralize to pH = 7 | 2523 | 5399.22 | 5008.56 | (−) 390.66 |
| | | | | MPS-V-009 | | | | |
| 4 | Soln-3 (10 ml) + Urea (0.50 g) | 1.26 | rt, 1 h | Filtrate (3 ml; pH = 7) | 2563 | 5484.82 | 2508.56 | (−) 2976.26 |

TABLE 3

MPS-V-003

| Entry | Soln compn | Amount of Reagent Used (g) | Reaction condn. | Analyzed portion of reaction mixture | Results (in mg/dL) | | | Amount of urea taken out (mg/dL/h) |
|---|---|---|---|---|---|---|---|---|
| | | | | | Blood Urea Nitrogen (BUN) | Blood Urea (BUN × 2.14) | Maximum amount of urea present | |
| 1 | Soln-3 (10 ml) Blank | — | — | — | 4 | 8.56 | 8.56 | — |
| 2 | Soln-3 (20 ml) + Urea (1.00 g) | | rt, 1 h | Filtrate (5 mL; pH = 1) | 2257 | 4740 | 5008 | 268.3 |
| 3 | Soln-3 (20 ml) + Urea (1.00 g) | | rt, 1 h | Filtrate (3 m; pH = 1) + saturated HCO3 (1 ml) to neutralize to pH = 7 | 1527 | 3267.78 | 5008 | 1740.22 |

TABLE 4

MPS-V-027 and MPS-V-036

| Entry | Soln compn | Amount of Reagent Used (g) | Reaction condn. | Analyzed portion of reaction mixture | Results (in mg/dL) | | | |
|---|---|---|---|---|---|---|---|---|
| | | | | | Blood Urea Nitrogen (BUN) | Blood Urea (BUN × 2.14) | Maximum amount of urea present | Amount of urea taken out (mg/dL/h) |
| 1 | Soln-4 Blank (9 ml) | — | — | — | 88 | 188.32 | 188.32 | — |
| 2 | Soln-4 (10 ml) + Urea (0.50 g) | MPS-V 036 (residue after filtration) (2.28 g) | rt, 1 h | Filtrate (2 ml) (pH = 6~7) | 0 | 0 | 2688.32 | 2688.32 |
| 3 | Soln-4 (10 ml) + Urea (0.50 g) | MPS-V 027 (residue after filtration and washing with MeOH) (4.40 g) | rt, 1 h | Filtrate (4 ml) (pH = 7~8) | 1114 | 2339.4 | 2688.32 | 349.3 |

TABLE 5

MPS-V-037, MPS-V-038 and MPS-V-047
Data for Solution -4

| Entry | Soln compn | Amount of Reagent Used (g) | Reaction condn. | Analyzed portion of reaction mixture | Results (in mg/dL) | | | |
|---|---|---|---|---|---|---|---|---|
| | | | | | Blood Urea Nitrogen (BUN) | Blood Urea (BUN × 2.14) | Maximum amount of urea present | Amount of urea taken out (mg/dL/h) |
| 1 | Soln-4 Blank (9 ml) | — | — | — | 25 | 53..5 | 53..5 | — |
| 2 | Soln-4 (20 ml) + Urea (1.00 g) | 2 | rt, 1 h | Filtrate (10 mL) (pH-7) | 0 | 0 | 5053.5 | 5053.5 |
| 3 | Soln-4 (10 ml) + Urea (0.50 g) | 13 (0.50 g) | rt, 1 h | Filtrate (10 mL) (pH-7) | 0 | 0 | 2553.5 | 2553.5 |
| 4 | Soln-4 (10 ml) + Urea (0.50 g) | MPS-V 047 (2.46 g) | rt, 1 h | Filtrate (5 ml) (pH = 5) | 479 | 1025.06 | 2553.5 | 1528.44 |

As will be appreciated from the foregoing, vinyl polymers having specific functional groups selected from carboxylic acids, esters and salts, amides, dicarboxylic acids, and esters and salts may be formulated to provide sorbents suitable for use in removing urea from an aqueous solution having a pH from about 6 to 8. Other sorbents suitable for removing urea form an aqueous solution having a pH range from 4 to 12 are realizable with various ones of the aforementioned specific functional groups by one of ordinary skill in the art having the information contained herein. Such exemplary polymers are substantially insoluble in water and can remove urea from dialysate at a rate of at least 2.5 mg/dl/hr. Additionally, such polymers may be soluble, substantially soluble or insoluble in water depending on variations in their manufacture.

In some variations of the invention, vinyl polymers such as polyvinyl alcohol, polyvinyl alcohol-ethylene co-polymers and polyacrylic acid are reacted with specific functional groups selected from carboxylic acids, carboxylic acid esters, carboxylates, amides, dicarboxylic acids, dicarboxylic acid esters, and dicarboxylates to produce the desired exemplary sorbents. Exemplary polymers may be applied to various substrates for use as dialysis sorbents. Such substrates may be organic or inorganic and may include filter paper, plastic or glass beads and other particulate materials that are insoluble in water. The polymers may also be applied to various screens and mesh-type filter materials formed from wire or plastic strands or cloth.

Another advantage of an exemplary urea sorbent is the use of selective functional groups that can be utilized to make a variety of resultant exemplary sorbents ranging from being soluble, insoluble, a liquid, a gum, an adhesive, a flexible material, a coating as well as a solid or powder.

It will be appreciated by those skilled in the art having the benefit of this disclosure that this urea sorbent provides a viable replacement for prior known dialysis sorbent materials. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A polymer suitable for use as a sorbent for regenerating dialysate, the polymer including specific functional groups bonded thereto that interact with urea in a liquid at a pH of between 6 and 8 to remove urea from an aqueous solution, wherein the polymer is substantially insoluble in water and reacts with urea without releasing ammonia and wherein the reaction product of the polymer and urea is substantially insoluble in water.

2. The polymer of claim 1, wherein the polymer comprises repeating units having the formula:

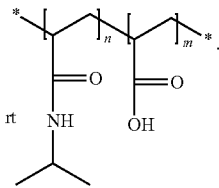

3. The polymer of claim 1, wherein the functional group comprises one of a carboxylic acid, a carboxylic acid ester, a carboxylate or amide.

4. A polymer suitable for use as a sorbent for regenerating dialysate, the polymer including specific functional groups bonded thereto that react with urea at a pH of between 4 to 12 to remove urea from an aqueous solution, wherein the polymer is either soluble or substantially insoluble in water and interacts or reacts with urea in a temperature range of about 50° F. to 110° F. without releasing ammonia and wherein the reaction product of the polymer and urea is soluble or substantially insoluble in water.

5. The polymer of claim 4, wherein the polymer comprises repeating units having the formula:

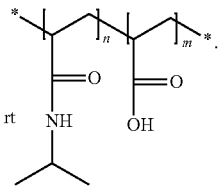

6. The polymer of claim 4, wherein the functional group comprises a carboxylic acid, a carboxylic acid ester, a carboxylate or amide.

* * * * *